United States Patent [19]
Einarsson

[11] Patent Number: 5,835,182
[45] Date of Patent: Nov. 10, 1998

[54] LENS-FREE ASSEMBLY FOR SHADING EYES FROM INCOMING LIGHT

[76] Inventor: Einar Th. Einarsson, Skeljanes 4, 101 Reykjavik, Iceland

[21] Appl. No.: 715,315

[22] Filed: Sep. 16, 1996

[51] Int. Cl.[6] .................................................. G02C 1/00
[52] U.S. Cl. ................................. 351/41; 2/12; 2/13
[58] Field of Search ........................ 351/41, 44, 63, 351/158; 2/12, 13

[56] References Cited

U.S. PATENT DOCUMENTS

| | | | |
|---|---|---|---|
| D. 104,294 | 4/1937 | Rentchler . | |
| D. 142,237 | 8/1945 | Goldberg | 57/1 |
| D. 161,885 | 2/1951 | Warner | 57/1 |
| D. 164,304 | 8/1951 | Houston | 57/1 |
| D. 172,120 | 5/1954 | Zuckerman | 57/1 |
| D. 178,711 | 9/1956 | Wells | 57/1 |
| D. 183,773 | 10/1958 | Spiezio | 57/1 |
| D. 196,000 | 8/1963 | McNeill | 57/1 |
| D. 197,418 | 1/1964 | Lissac | 57/1 |
| D. 209,780 | 1/1968 | Shindler | 57/1 |
| D. 284,867 | 7/1986 | Takatsuji | 16/123 |
| D. 354,974 | 1/1995 | Wielhouwer | 16/301 |
| D. 358,828 | 5/1995 | Jannard et al. | 16/101 |
| D. 367,667 | 3/1996 | Simioni et al. | 16/315 |
| 779,340 | 1/1905 | Wynkoop | 2/13 |
| 1,289,227 | 12/1918 | Moore | 2/13 |
| 1,310,077 | 7/1919 | Heaford . | |
| 1,528,282 | 3/1925 | White . | |
| 1,706,682 | 3/1929 | Takacs . | |
| 1,917,900 | 7/1933 | Redman . | |
| 2,286,269 | 6/1942 | Gilmartin | 2/12 |
| 2,382,962 | 8/1945 | Courtney | 88/41 |
| 2,456,334 | 12/1948 | Shindel | 2/14 |
| 2,603,783 | 7/1952 | Gilmartin | 2/12 |
| 3,020,552 | 2/1962 | Coon | 2/15 |
| 3,233,249 | 2/1966 | Baratelli et sl. | 2/14 |
| 3,531,189 | 9/1970 | Petito | 351/90 |
| 3,756,704 | 9/1973 | Marks | 351/60 |
| 4,998,815 | 3/1991 | Lin | 351/106 |
| 5,321,443 | 6/1994 | Huber et al. | 351/47 |
| 5,428,410 | 6/1995 | Lei | 351/47 |
| 5,640,218 | 6/1997 | Kanda | 351/63 |

FOREIGN PATENT DOCUMENTS

| | | |
|---|---|---|
| MR 0482 | 6/1997 | Denmark . |
| 138298 | 4/1997 | Spain . |
| NR 61946 | 10/1997 | Sweden . |
| 2054947 | 7/1996 | United Kingdom . |

Primary Examiner—Hung X. Dang
Attorney, Agent, or Firm—Sofer & Haroun, LLP

[57] ABSTRACT

A device for protecting the eyes by preventing incoming sunlight from falling upon the eyes includes a lens-free eye shade frame having detachable and interchangeable shades of different sizes and shapes attached to the frame and biased outward and extending horizontally from a wearer's face. The eye shade frame includes biasing members arranged on the front portion of the frame just above the wearer's eyes proximate the wearer's eyebrows for permitting adjustment of the shades on the frame by the wearer. The biasing members have engaging ends which are wedge shaped such that shades which engages the biasing members are biased horizontally outward from the wearer's face and are resiliently retained on the frame. The eye shade frame includes rearwardly extending ear extensions attached to the front portion of the frame which may be inwardly foldable. The foldability of the eyeshade frame and the resilient attachment of the shades to the frame permit easy storage in a case despite the outward arrangement of the shades on the frame.

17 Claims, 6 Drawing Sheets

LENS-FREE ASSEMBLY FOR SHADING EYES FROM INCOMING LIGHT

FIELD OF THE INVENTION

This invention relates to eye shades, and in particular, to an eye shade assembly having shades disposed on a frame for preventing incoming sunlight from striking a wearer's eyes.

BACKGROUND OF THE INVENTION

The glaring rays of incoming sunlight are often extremely distracting and may be painful to some people. To reduce or block out as much of this distracting sunlight as possible, individuals generally resort to sunglasses with colored or tinted protective lenses, or attachments for eyeglasses which have the same protective colored or tinted lenses. However, sunglasses or eyeglass attachments with protective lenses are often expensive and may require a prescription for those with less than perfect vision. Additionally, many individuals find the colors and the shapes of the lenses on the sunglasses annoying, unattractive, and oftentimes a hindrance to their natural vision. Furthermore, wearer's of contact lenses who shun glasses for cosmetic purposes may not wish to wear sunglasses over their contact lenses. Moreover, many wearers of color contact lenses find that the use of sunglasses or eyeglass attachments having colored lenses impair their vision when the glasses are worn in addition to the contact lenses. Athletes, for example, such as baseball or softball players may not desire to wear sunglasses, since the weight of the glasses and/or tint of the lenses, may hinder their ability to see the ball.

The prior art is replete with references disclosing sunglasses and devices for attachment to eyeglasses for thwarting the distracting rays of the sun from reaching one's eyes.

U.S. Pat. No. 2,603,783 and U.S. Pat. No. 2,286,269, both to Gilmartin, generally recite removable eye shade attachments for placement upon a pair of conventional eyeglasses. The attachments in the U.S. Pat. No. 2,603,783 reference, however, are made removable through the use of screws which fix the attachment to the wearer's glasses, while the attachments disclosed in the U.S. Pat. No. 2,286,269 reference are held in place in slots formed in the eyeglass frame. One disadvantage with these eye shades is that it is difficult to secure or to remove these frames from a wearer's eyeglasses. Furthermore, when the shading portions are fixed to the eyeglasses, they cannot be biased at an angle to obtain the maximum protection from the sun.

U.S. Pat. No. 1,528,282 to White recites two independent canopies or shades detachably mounted on a wire frame. However, these canopies are fixed, extend laterally outward from the frame, and cannot be biased at an angle to obtain the maximum protection from the sun. Additionally, since the shades are fixed, they may not be rotated or adjusted for storage in a case. Furthermore, in order to mount the shades on the frame, the frame must be bent. Repeated bending of the frame to change or clean the shades may eventually cause the frame to break.

U.S. Pat. No. 2,456,334 to Shindel discloses a protective goggle having a lens unit of flexible plastic sheet attached to a mounting frame, the lens unit being disposed in front of the wearer's eyes. However, the lens unit is large and bulky and may easily disengage from the mounting frame while being worn.

U.S. Pat. No. 5,321,443 to Huber et al. recites a removable sunglass assembly which is removably attachable to a pair of conventional eyeglasses to block out the distracting sunlight and protect the eyes from the glare of the incoming rays. This attachment is extremely large and requires numerous steps for attaching to a pair of eyeglasses. Additionally, this attachment is prone to loosening and may slip off the eyeglasses to which they are attached.

As an alternative to those who do not wish to wear sunglasses or place attachments on their eyeglasses, many hats are provided with elongated visors or "bills" which extend horizontally from the hat while on the wearer's forehead. The visor provides a blockage surface which prevents the sunlight from striking the eyes and shades the eyes from the sun, allowing the individual to see naturally without any tinted or colored lenses in front of his or her eyes. However, many people do not enjoy wearing hats. In addition, the hat visor is generally situated at the top of the wearer's forehead distant from the wearer's eyes, thus permitting a substantial amount of light to seep around the visor. Furthermore, since the visor is generally fixed to the hat and hence unadjustable, it is often improperly angled for deflecting the maximum amount of sunlight possible. As a result, distracting sunlight may extend past the visor and reach the wearer's eyes.

Hats with visors are not just for outdoor wear, however. Many painters and construction workers wear hats with visors to keep debris or paint from falling in their eyes, as when painting or building a ceiling. However, many painters and construction workers find hats uncomfortable, or find that wearing hats interfere with their ability to see the ceiling, and hence shun wearing hats altogether, thus exposing their eyes to falling debris or dripping paint.

Accordingly, there is a need for an eye shade which is lightweight, inexpensive, attractive and stylish, and which does not hinder natural vision by the use of lenses, yet which prevents sunlight from falling upon the eyes.

OBJECTS AND SUMMARY OF THE INVENTION

It is thus a general object of the present invention to provide a lens-free eye shade assembly having a frame configured for preventing incoming sunlight from striking a wearer's eyes.

It is an additional object of the present invention to provide a lens-free eye shade assembly having a frame configured to receive shading members thereon such that the shading members shade the wearer's eyes and provide a barrier which prevents incoming sunlight from striking the wearer's eyes.

A more specific object of the present invention is to provide a lens-free eye shade assembly having a biasing member disposed on a frame for resiliently retaining shading members thereon in an outward and substantially horizontal manner.

It is another object of the present invention to provide a lens-free eye shade assembly in which the shading members are detachable from the frame and interchangeable.

It is another object of the present invention to provide a lens-free eye shade assembly which may utilize a variety of different shaped shading members.

It is a further object of the present invention to provide a lens-free eye shade assembly in which the frame is hinged and which is storable in a storage case.

In accordance with one aspect of the present invention, a lens-free eye shade assembly is provided with a frame having a front portion which lies in front of the wearer's face and extends just above the eyes proximate the wearer's eyebrows. To retain the frame on the wearer's face, a nose piece is attached to the front portion for resting the frame on the wearer's nose. Additionally, ear extensions are hingedly attached to the front portion of the frame and extend rearward from the front portion for placement behind a wearer's ears. At least two a biasing members are provided on the front portion of the frame for retaining shading members on the frame. Each biasing member includes engaging ends which are generally wedge-shaped and angled such that shading members which engage the engaging ends of the biasing members when placed on the front portion of the frame, are biased outward and substantially horizontal from the frame. The shading members are replaceable eye shades and are provided in a variety of shapes and sizes for interchangeability on the frame. The eye shades include slotted bores for easily attaching and removing the eye shades from the frame. The bores are disposed on opposite ends of the eye shades at points such that the width between the bores on the eye shades is preferably greater than the distance between the biasing members on the frame so that the eye shades become slightly flexed and rotatable when positioned against the engaging end of the biasing members on the frame. This rotatability of the eye shades on the frame, in conjunction with the hinged attachment of the ear extension to the front portion of the frame renders the eye shade assembly collapsible for easy storage in a storage case.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

DETAILED DESCRIPTION OF THE DRAWINGS

In the drawings in which like reference characters denote similar elements throughout the several views.

DETAILED DESCRIPTION OF THE PRESENTLY PREFERRED EMBODIMENT

Figure 3:
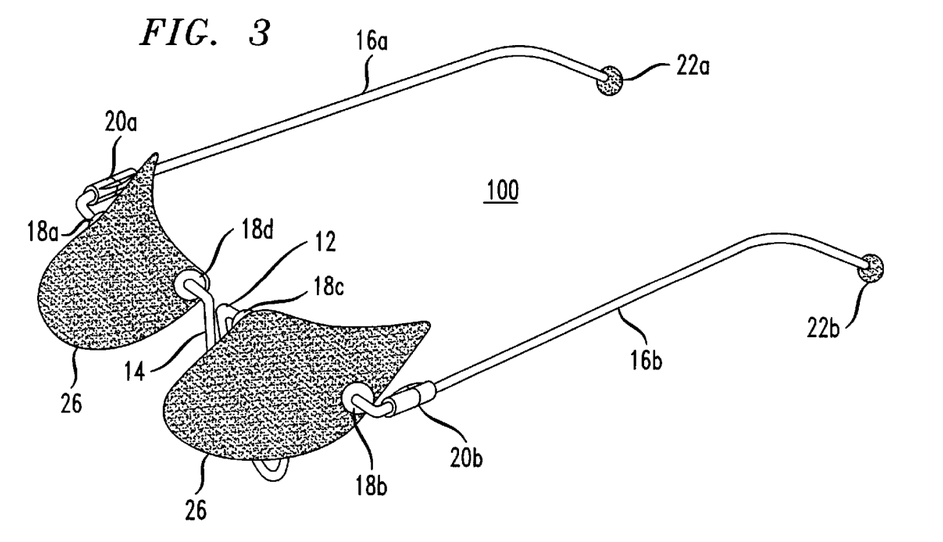
FIG. 3 illustrates a perspective view of the preferred embodiment of the eye shade assembly of the present invention with attached eye shades.

With initial reference to FIG. 3, there is shown one embodiment of the eye shade assembly 100 according to the present invention. The eye shade assembly 100 comprises, preferably, a pair of replaceable eye shading members 26 and a frame 10, which is employed to hold the eye shading members 26 at a given angle. Various elements of the eye shade assembly 100 are described in further detail hereinafter.

Figure 1:
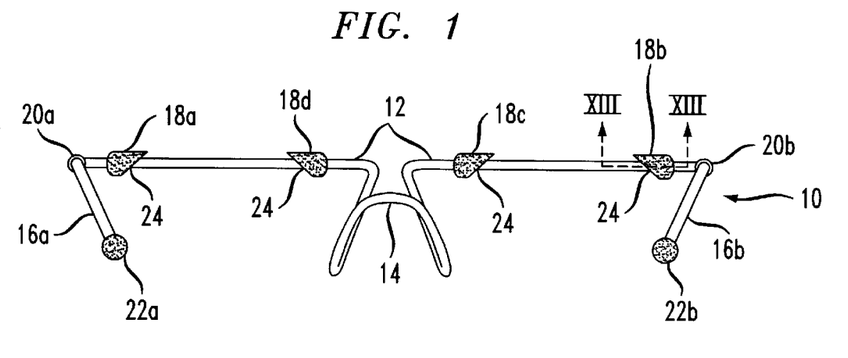
FIG. 1 illustrates an elevational view of the preferred embodiment of the eye shade frame of the present invention viewed from the rear and having two pairs of biasing members.
Figure 2:
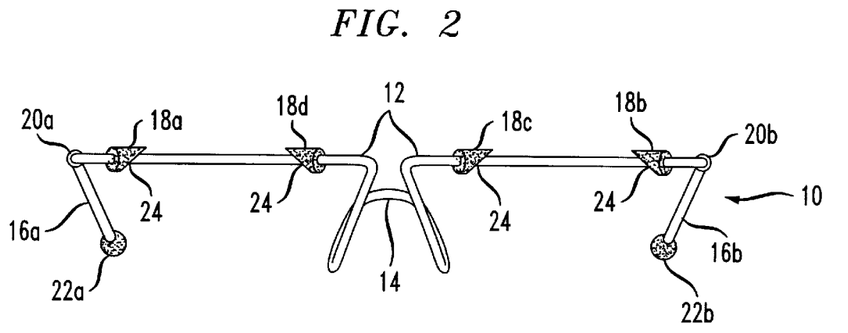
FIG. 2 illustrates an elevational view of the preferred embodiment of the eye shade frame of the present invention viewed from the front and having two pairs of biasing members.
Figure 7:
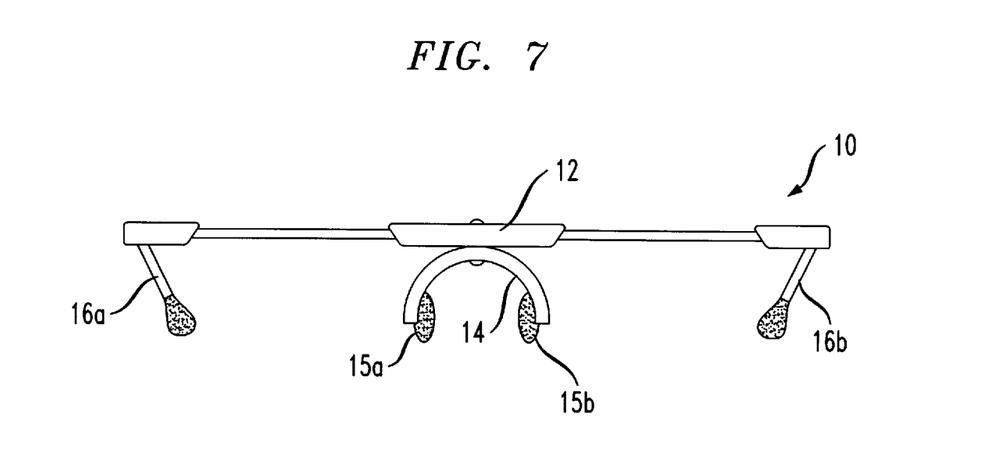
FIG. 7 illustrates a frontal view of an alternative embodiment of the eye shade frame of the present invention illustrating the attached nose piece with cushioning means.

FIGS. 1 and 2 illustrate one embodiment of the eye shade frame 10 of the present invention, although the invention is not limited in scope to this embodiment. As illustrated, frame 10 is comprised of front portion 12, a pair of ear extensions 16a, 16battached to front portion 12 via hinges 20a, 20b such that ear extensions 16a, 16b are foldable inwardly. The invention is not, however, limited to the use of hinges, and other means of attachment may be utilized and which function equally well. Ear extensions 16a, 16b extend rearwardly from said front portion 12 for placement behind a wearer's ears, and may be straight as illustrated in FIGS. 1 and 2, or curved at the portion which extends behind the wearer's ear as shown in FIG. 3. A nose piece 14 extends from front portion 12 of frame 10 at its center point, and may be integral with frame 10 as illustrated in FIGS. 1 and 2. Alternatively, as shown in FIG. 7, nose piece 14 may be attached to frame 10 by any suitable means such as glue, welding or screws, and may optionally be provided with cushioning pads 15a, 15b for added comfort.

Figure 4:
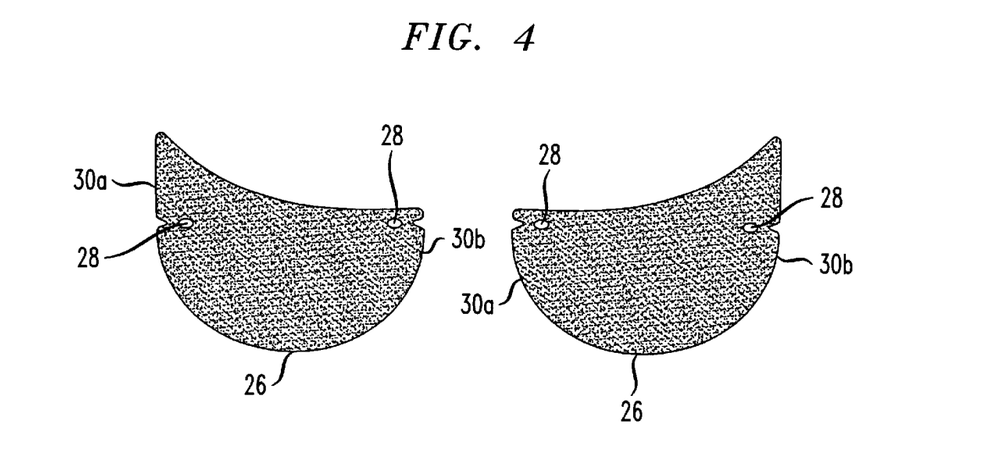
FIG. 4 illustrates one embodiment of the shading members according to the present invention including a pair of eye shades.
Figure 8:
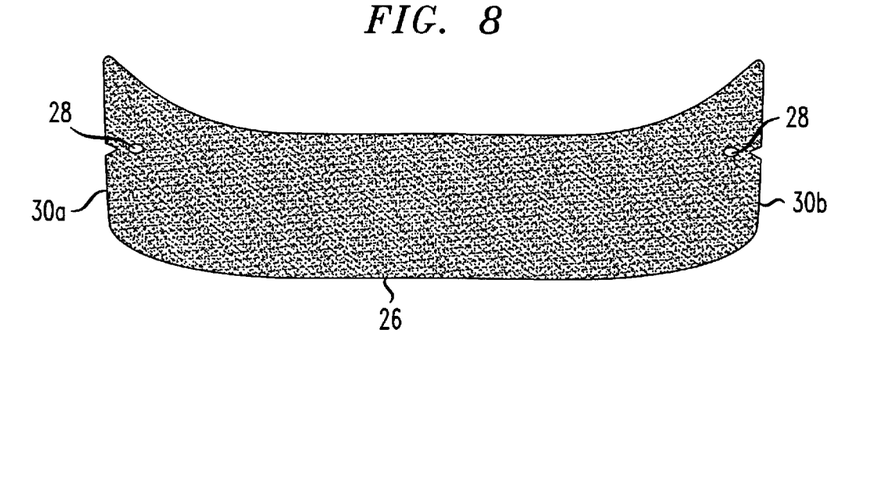
FIG. 8 illustrates an alternative embodiment of the shading member according to the present invention including a single eye shade.
Figure 9:
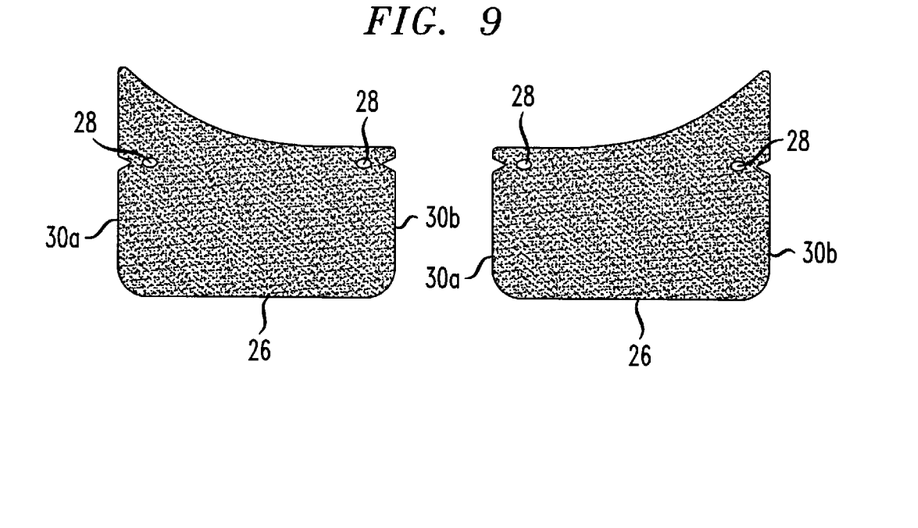
FIG. 9 illustrates an alternative embodiment of a the shading members according to the present invention including a pair of eye shades.

Frame 10 is preferably a unitary bent-wire frame configured in the form of normal eyeglasses absent the viewing lenses. Those skilled in the art will realize that frame 10 may be comprised of a variety of other materials such as plastic. Shading members 26, in the form of replaceable eyeshades, as illustrated in FIGS. 3–6, are provided for placement on front portion 12 of frame 10 for blocking the path of sunlight to the wearer's eyes. Shading members 26 which may be configured in a variety of shapes, as shown in FIGS. 4, 8, and 9, are preferably opaque and comprised of die-cut flexible plastic, although other materials such as sheet metal and cardboard may work as well.

The shading members 26 include at least one set of opposite ends 30a and 30b, upon each end of which a slotted bore 28 is disposed therethrough. Shading members 26 are preferably releasably attached to front portion 12 of frame 10 via slotted bores 28, and fit around frame 10 for easy removal and interchangeability with shading members of other shapes and/or sizes. Shading members 26 are resiliently retained on frame 10 by a plurality of biasing members 18a–18d (shown in FIGS. 1 and 2) which are disposed on front portion 12 of frame 10 on the area which correspond to a wearer's eyes when frame 10 is placed on a wearer's face.

Figure 5:
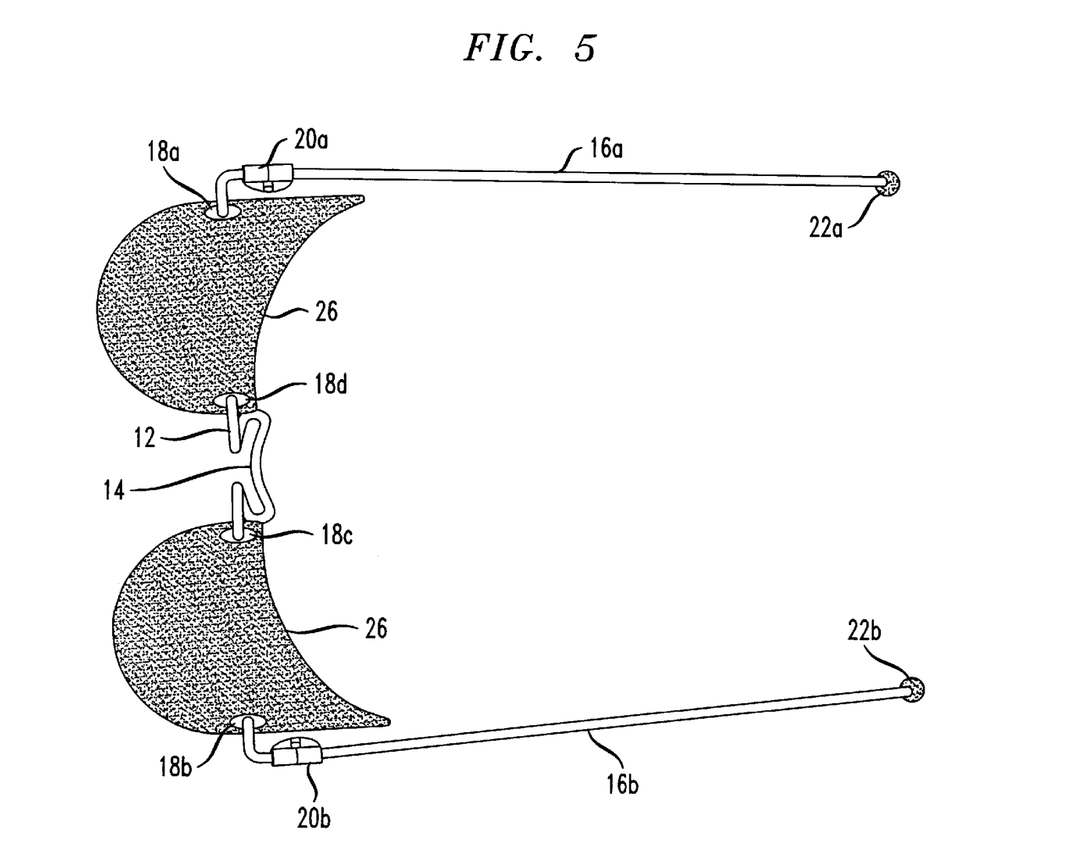
FIG. 5 illustrates a top plan view of the preferred embodiment of the eye shade assembly with attached eye shades.
Figure 6:
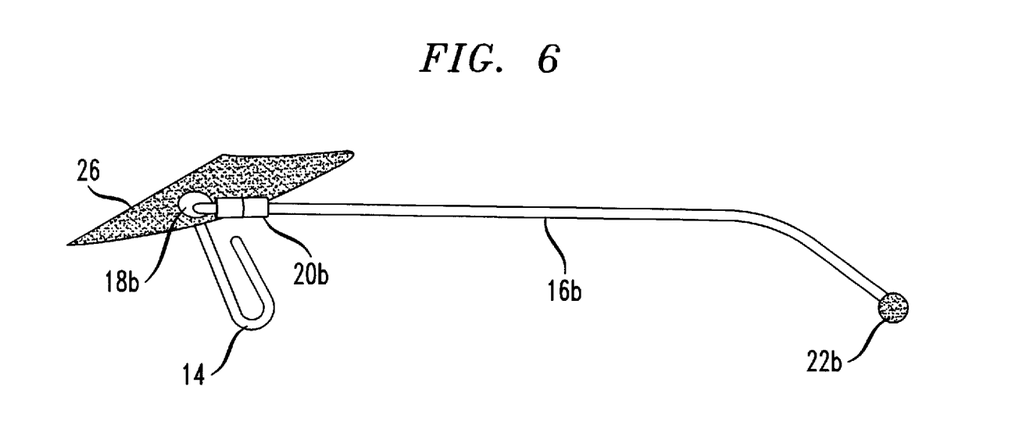
FIG. 6 illustrates a side view of the preferred embodiment of the eye shade assembly with attached eye shades.
Figure 10:
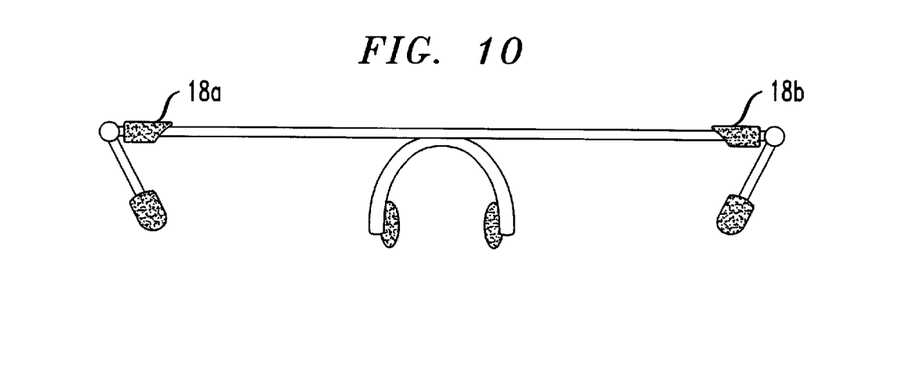
FIG. 10 illustrates an elevational view of an alternative embodiment of the eye shade frame of the present invention viewed from the from and having only one pair of biasing members.

Advantageously, shading members 26 are sized and configured such that a portion of the shading member 26 extends above frame 10 to prevent light from seeping behind frame 10 and reaching the wearer's eyes. As shown in the preferred embodiment of the present invention in FIGS. 1–3, biasing members 18a and 18c are paired together, as are biasing members 18b and 18d, for retaining two independent shading members 26 on frame 10 as illustrated in FIGS. 3 and 5, although one pair of biasing members 18a, 18b may be utilized as shown in an alternative embodiment of frame 10 in FIG. 10 for retaining a single shading means 26 as illustrated in FIG. 8. As illustrated, slotted bores 28 of shading members 26 are located such that the width between the bores 28 and the shading members is preferably greater than the distance between the biasing members 18 and the frame 10 so that shading members 26 become slightly flexed and rotatable when positioned against biasing members 18 on frame 10. To this end, slotted bores 28 on the shading members 26 are advantageously elliptical in shape such that when the shading members 26 are mounted on frame 10, the elliptical bore forms a circle such that the shading members 26 may be rotated on frame 10 with minimal friction.

Figure 11A:
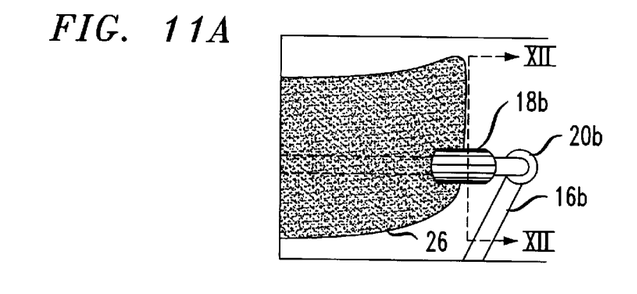
FIG. 11a illustrates an enlarged view of a biasing member according to the present invention having a shading members engaged therewith.
Figure 11B:
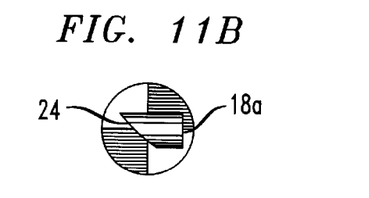
FIG. 11b illustrates a side view of a biasing member according to the present invention.
Figure 11C:
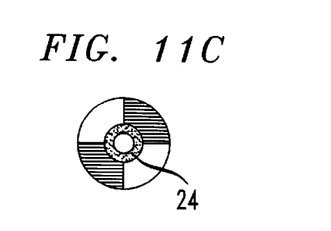
FIG. 11c illustrates a front view of a biasing member according to the present invention.
Figure 12:
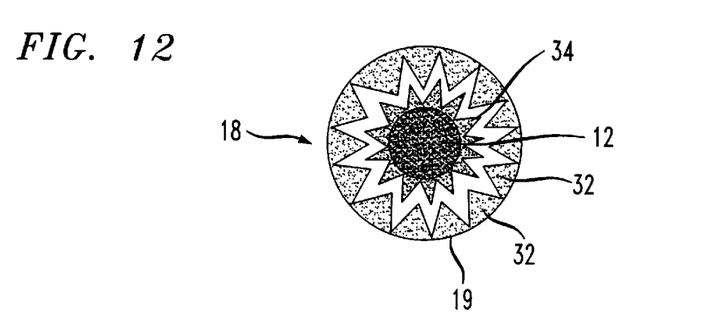
FIG. 12 illustrates an enlarged cross-sectional view of the biasing member according to the present invention viewed along line XII—XII in FIG. 11, having interlocking teeth for permitting digital rotation on the frame.
Figure 13:
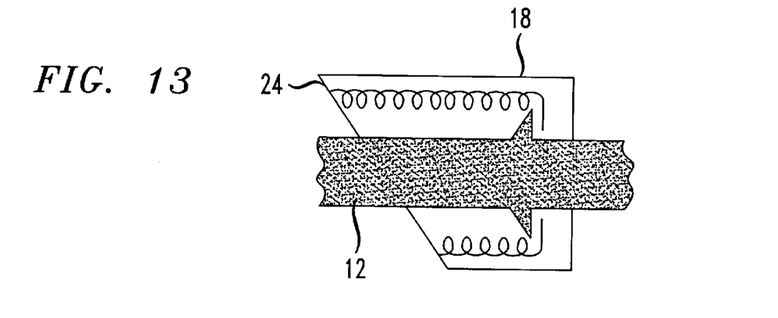
FIG. 13 illustrates a cross-sectional view of the biasing member according to the present invention viewed along line XIII—XIII in FIG. 1 and having a spring lock mechanism for permitting digital rotation on the frame.

Biasing members 18a–18d, as in FIGS. 1 and 2, and shown enlarged and in greater detail in FIG. 11 are provided with eye shade engaging ends 24 in the shape of a wedge so as to bias shading members 26 at a predetermined angle such that shading members 26 are rotatable on front portion 12 of frame 10 and resiliently biased outward and extend horizontally from front portion 12 of frame 10 as shown in FIG. 3. The wedge shape of the eye shade engaging ends, permits shading members 26 on front portion 12 of frame 10 to be partially rotated thereon, but prevents full rotation and resiliently returns shading members 26 to their optimal horizontally outward angle for preventing sunlight from striking the wearer's eyes. It is noted that the alignment of wedge-shaped engagement ends 24 on front portion 12 of frame 10 can advantageously be altered so that the shading members 26 can be biased at a desired angle. For example, as shown in FIG. 12, biasing member 18 may be provided with digital teeth 32 circumferentially disposed about its interior 19. Front portion 12 of frame 10 may be provided with complementary interlocking teeth such that biasing member 18 may be digitally rotated on frame 10 to position shading members 26 at a desired angle in relation to the wearer's eyes. Alternatively, as illustrated in FIG. 13, biasing member 18 may be provided with a spring lock mechanism 36 such that pushing or pulling biasing member 18 while turning along frame 10 permits adjustment of the wedge-shaped engagement ends 24 of biasing member 18 wherein shading members 26 may be angled according to the wearer's preference. The invention is not, however, limited in these adjustment mechanisms, and those skilled in the art will realize that other methods of adjustment may be utilized.

Figure 14:
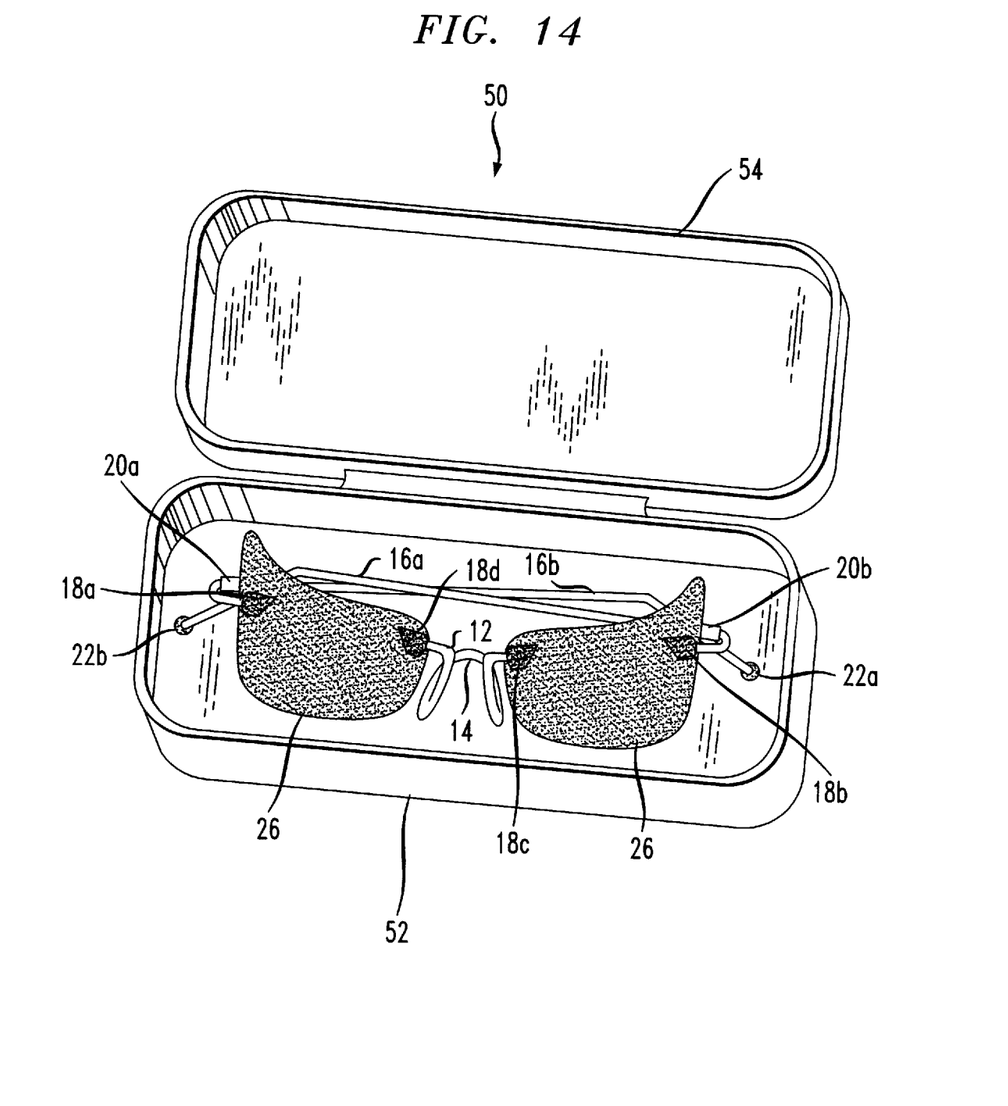
FIG. 14 illustrates the eye shade assembly with attached shading members according to the present invention in collapsed form and placed within a case for storage.

As shown in FIG. 14, a case 50 is provided with a base portion 52 and a closing cover portion 54 and is configured for storing frame 10 when not being worn by a wearer. By folding ear extensions 16a and 16b inward, frame 10 may be compactly placed in base portion 52 of case 50. While frame 10 is in the box, shading members 26 remain extended outward and away from the case 50. However, since shading members 26 are resilient and rotatable when engaged with eye shade engaging ends 24 of biasing members 18a–18d, cover portion 54 of case 50 may be shut causing the shading members 26 to rotate to an inward position to prevent damaging the outwardly extending shading members 26.

It is noted that in addition to the many features explained above, in accordance with one aspect of the present invention, it is possible to place text or artwork on shading members 26. For example, by placing a company brand name or logo on shading members 26, the eye shade assembly of the present invention can advantageously function as an attractive brand product.

Thus, while there have been shown and described and pointed out fundamental novel features of the invention as applied to preferred embodiments thereof, it will be understood that various omissions and substitutions and changes in the form and details of the disclosed invention may be made by those skilled in the art without departing from the spirt of the invention. It is the intention, therefore, to be limited only as indicated by the scope of the claims appended hereto.

It is to be understood that the drawings are not necessarily drawn to scale, but that they are merely conceptual in nature.

What is claimed is:

1. An eye shade frame to be worn upon a wearer's face for blocking incoming sunlight, comprising:

a front portion extending substantially parallel with the forehead of the wearer;

a nose piece, said nose piece attached to said front portion of said frame such that said frame may rest upon the wearer's nose;

ear extensions having a first end and a second end, said ear extensions directed rearwardly from said front portion for placement behind a wearer's ear for providing support to securely retain said frame on the wear's face;

shading members with bores therethrough for arrangement on said front portion of said frame, said bores positioned proximate said biasing members such that said shading members are biased outward in a plane horizontal with the wearer's forehead so as to prevent sunlight from striking the wearer's eyes, said bores having a corresponding slit such that said shading members are releasably engageable with said frame, ; and at least two biasing members disposed on said front portion for rotatably and resiliently retaining said shading members thereon.

2. The eye shade frame of claim 1, wherein said bores are shaped as ellipses, such that when said shading members are mounted on said front portion of said frame said elliptical bores form the shape of a circle wherein said shading members on said frame rotate with substantially no friction.

3. The eye shade frame of claim 1, wherein said shading members comprise a pair of said shades being positioned on said front portion of said frame above the wear's eye.

4. The eye shade frame of claim 3, wherein said shades are opaque to block incoming sunlight from striking the wearer's eyes.

5. The eye shade frame of claim 3, wherein said shades are flexible die-cut plastic.

6. The eye shade frame of claim 3, wherein said shades are semi-circular.

7. The eye shade frame of claim 3, wherein said shades are round.

8. The eye shade frame of claim 3, wherein said shades are ovular.

9. The eye shade frame of claim 3, wherein said shades are rectangular.

10. The eye shade frame of claim 1, wherein said shading members comprise a single shade disposed on said front portion of said frame such that said shade prevents incoming sunlight from striking a wearer's eyes.

11. A replaceable eye shade engageable with an eye shade frame having at least two spaced apart biasing members disposed on said eye shade frame, said replaceable eye shades comprising:

a surface having two opposite ends, each of said opposite ends having a bore therethrough, said bores positioned proximate said biasing members such that said shading members are biased outward in a plane substantially horizontal with the wearer's forehead, so as to prevent sunlight from striking the wear's eyes.

12. The replaceable eye shade of claim 11, wherein said bores are shaped as ellipses, such that when said shading members are mounted on said front portion of said frame said elliptical bores form the shape of a circle wherein said shading members on said frame rotate with substantially no friction.

13. An eye shade assembly for blocking incoming sunlight, said eye shade assembly comprising:

a frame, to be worn upon a wearer's face, said frame having:
  a front portion extending parallel with the forehead of the wearer;
  a nose piece attached to said front portion of said frame such that said frame may rest upon the wearer's nose;
  ear extensions having a first end and a second end, said ear extensions directed rearwardly from said front portion for placement behind a wearer's ear for providing support to securely retain said frame on the wearer's face;

at least two biasing members disposed on said front portion of said frame;

shading members, said shading members comprised of a surface having at least one pair of opposite sides, each of said opposite sides having a bore therethrough, said bores positioned proximate said biasing members on said eye shade frame such that said surface is retained on front portion of said eye shade frame and biased outward and substantially horizontally from said eye shade frame; and a storage box configured to receive said eye shades for storage therein, said box having a folding door further configured to define an open and closed position, such that when said door is in said closed position said shading members rotate to fit inside said box.

14. The eye shade assembly of claim 13, wherein said frame further comprising a set of hinges, said hinges connecting said front portion and said first end of said rearwardlyextending ear extensions, such that said ear extensions may be folded inward for storage.

15. The eye shade assembly of claim 13, wherein said biasing members have an eye shade engaging end in the shape of a wedge so as to bias said shading members at said given angle.

16. The eye shade assembly of claim 13, wherein said eye shade engaging end is aligned at an angle such that said shading members are biased outward and substantially horizontally from said frame.

17. The eye shade assembly of claim 13, herein said bores on said surface of said shading members are shaped as ellipses, such that when said shading members are mounted on said front portion of said frame said elliptical bores form the shape of a circle wherein said shading members on said frame rotate with substantially no friction.

* * * * *